United States Patent [19]

Letterio

[11] Patent Number: 4,572,212
[45] Date of Patent: * Feb. 25, 1986

[54] SUBARACHNOID BOLTS

[75] Inventor: Fred Letterio, Philadelphia, Pa.

[73] Assignee: Paul L. Sweeney, Jr., Laurel Springs, N.J.

[ * ] Notice: The portion of the term of this patent subsequent to Mar. 27, 2001 has been disclaimed.

[21] Appl. No.: 555,460

[22] PCT Filed: Mar. 15, 1983

[86] PCT No.: PCT/US83/00347
§ 371 Date: Nov. 3, 1983
§ 102(e) Date: Nov. 3, 1983

[87] PCT Pub. No.: WO83/03190
PCT Pub. Date: Sep. 29, 1983

Related U.S. Application Data

[63] Continuation-in-part of Ser. No. 358,444, Mar. 15, 1982, Pat. No. 4,438,773.

[51] Int. Cl.⁴ .............................................. A61B 5/00
[52] U.S. Cl. .................................. 128/748; 128/303 R
[58] Field of Search ............... 128/748, 303 R, 303 B; 604/93, 175

[56] References Cited

U.S. PATENT DOCUMENTS 4,062,354 12/1977 Taylor et al. .................... 128/748 X
4,186,728 2/1980 van Lofringen ................ 128/748 X

FOREIGN PATENT DOCUMENTS 2384482 11/1978 France ................................. 128/748
7801416 9/1978 Netherlands ........................ 128/748

Primary Examiner—Lee S. Cohen
Assistant Examiner—Angela D. Sykes
Attorney, Agent, or Firm—Duffield & Lehrer

[57] ABSTRACT

A subarachnoid bolt for use in measuring intracranial pressure includes a lower bolt half and an upper bolt half which can be screwed to the lower bolt half. A tubular member extends downwardly from the lower bolt half and is adapted to be inserted into a hole formed in a patient's skull. In one embodiment, the bolt is securely held in place when the free end of a tubular element carried by the upper bolt half enters the tubular member and cams the lowermost end thereof radially outwardly when the two bolt halves are screwed together. In a second embodiment, a sleeve on the lower bolt half bulges outwardly against the walls of the hole when the two bolt halves are screwed together.

7 Claims, 8 Drawing Figures

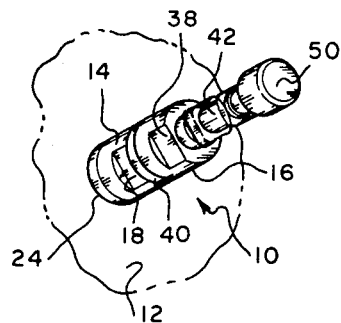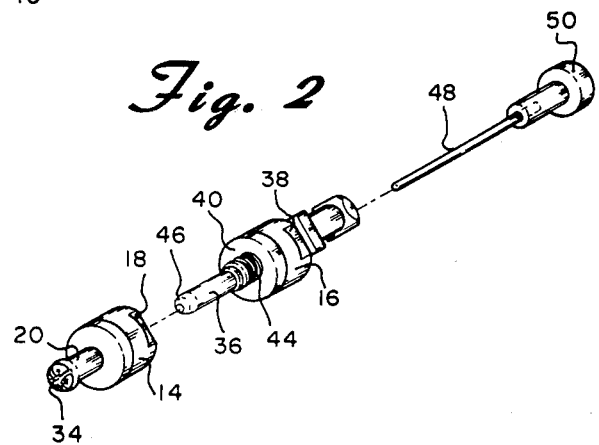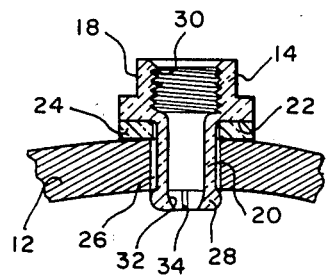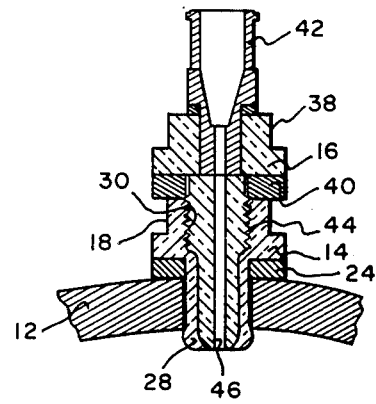

SUBARACHNOID BOLTS

CROSS-REFERENCE TO RELATED APPLICATION

This application is a continuation-in-part of prior application Ser. No. 358,444, filed Mar. 15, 1982, now U.S. Pat. No. 4,438,773.

TECHNICAL FIELD

The present invention is concerned with the measurement of intracranial pressure. Several devices have been utilized to perform such measurements. These include intraventricular catheters, subarachnoid bolts and solid state or implantable transducers. This invention relates to improvements in subarachnoid bolts.

BACKGROUND ART

Subarachnoid bolts for measuring or monitoring intracranial pressure have been known for some time. One of the more widely utilized bolts, commonly referred to as a "Philly" bolt, is comprised essentially of stainless steel or similar material and includes an external screw thread at its lower end which is intended to be screwed into a twist drill hole formed in a patient's skull. The extreme end of the bolt enters the subarachnoid space over the cerebral hemisphere.

While known subarachnoid bolts have met with some success, they have also suffered from many problems particularly with patients with very thin skulls such as neonatal patients. With such patients and in many other cases, it is extremely difficult and sometimes impossible to secure the bolt to the skull by screwing the same thereto.

DISCLOSURE OF INVENTION

The present invention overcomes the defects of the prior art known to Applicant and provides a subarachnoid bolt which can be easily secured to substantially any skull. The bolt of the present invention includes a lower bolt half and an upper bolt half which can be screwed to the lower bolt half. A tubular member extends downwardly from the lower bolt half and is adapted to be inserted into a hole formed in a patient's skull. In one embodiment, the bolt is securely held in place when the free end of a tubular element carried by the upper bolt half enters the tubular member and cams the lowermost end thereof radially outwardly when the two bolt halves are screwed together. In a second embodiment, a sleeve on the lower bolt half bulges outwardly against the walls of the hole when the two bolt halves are screwed together.

BRIEF DESCRIPTION OF DRAWINGS

For the purpose of illustrating the invention, there are shown in the accompanying drawings forms which are presently preferred; it being understood that the invention is not intended to be limited to the precise arrangements and instrumentalities shown.

FIG. 1 is a perspective view of a subarachnoid bolt constructed in accordance with the principles of the present invention;

FIG. 2 is an exploded perspective view of the bolt shown in FIG. 1;

FIG. 3 is a cross-sectional view of the lower bolt half inserted in a hole in a patient's skull;

FIG. 4 is a cross-sectional view of the bolt secured to a patient's skull;

BEST MODE FOR CARRYING OUT THE INVENTION

Figure 5:
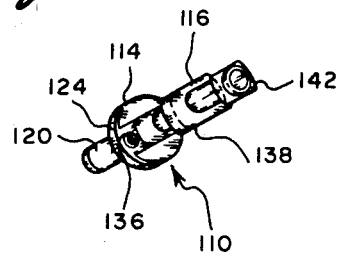
FIG. 5 is a perspective view of a second embodiment of a subarachnoid bolt according to the invention.
Figure 6:
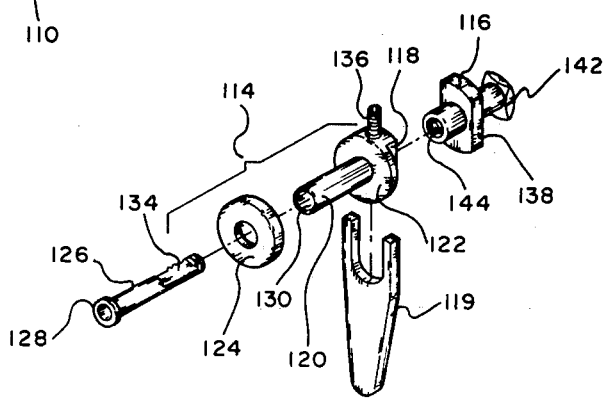
FIG. 6 is an exploded perspective view of the bolt shown in FIG. 5.

Referring now to the drawings in detail wherein like reference numerals have been used throughout the various figures to designate like elements, there is shown in FIG. 1 a first embodiment of subarachnoid bolt constructed in accordance with the principles of the present invention and designated generally as 10. In FIG. 1, bolt 10 is shown secured to the skull 12 of a patient.

Bolt 10 is comprised of two parts: a lower bolt half 14 and an upper bolt half 16. As shown most clearly in FIGS. 2 and 3, lower bolt half 14 is essentially circular in cross section except for the upper portion thereof which is squared as shown at 18 to form a means by which a wrench or similar tool can hold the lower bolt half 14 to prevent the same from rotating. The reason for this will become more readily apparent hereinafter.

The lower section of lower bolt half 14 is reduced in diamter and forms a tubular member 20 which is coaxially aligned with the remaining parts of the bolt. An enlarged flange 22 is thereby formed above the tubular member 20. A sealing washer 24 rests against the flange 22 and around the upper part of the tubular member 20.

As shown most clearly in FIG. 3, the tubular member 20 is adapted to be inserted into a substantially complementary shaped hole 26 in a patient's skull 12. The length of the tubular member 20 is selected so that the lowermost end 28 thereof which is slightly bulbous lies just below the lowermost surface of the skull 12. The flange 22 and washer 24 overlie the outer surface of the skull 12 around the hole 26.

Lower bolt half 14 is substantially hollow, having a channel passing entirely therethrough. An internal screw thread 30 is formed in the uppermost part and the inner surface of the lowermost end 28 is substantially conically shaped as shown at 32. The wall of the lowermost end 28 of the tubular member 20 also includes a plurality of axially extending slits 34 therein. In the preferred embodiment of the invention, four such slits are shown (see FIG. 2). This is by way of example only as the invention could function with fewer or more such slits. The purpose of the slits 34 is to weaken the wall of the lowermost end portion 28 slightly so that the same can be flexed outwardly when the bolt is in use as will be explained more clearly hereinafter. With the end portion 28 flexed outwardly, the bulbous portion forces against the undersurface of the skull 12 to retain the bolt in place.

The details of the upper bolt half 16 are shown most clearly in FIGS. 2 and 4. As with the lower bolt half 14, the upper bolt half 16 has a main body portion with a concentrically arranged tubular element 36 extending downwardly therefrom. A squared section 38 similar to section 18 also allows the upper bolt half to be held by a wrench or similar tool so that the same can be turned relative to the lower bolt half. A washer 40 similar to washer 24 extends around the uppermost part of the tubular element 36. The uppermost part of the upper bolt half 16 carries a coaxially arranged adapter or connector 42 which is utilized for connecting the bolt to remotely located sensing and/or measuring equipment.

An external screw thread 44 is formed on the upper end of the tubular element 36. This screw thread 44 is complementary to the screw thread 30 on the lower bolt half 14 so that the two bolt halves can be secured together with the tubular element 36 entering the interior of the lower bolt half 14. The forwardmost end 46 of the tubular element 36 is also substantially conically shaped and as the two bolt halves are screwed together, this end 46 moves downwardly and pushes against the conical inner surface 32 to cam the lower end 28 of the lower bolt half 14 outwardly to secure the bolt in place. A conventional pin 48 with handle 50 may also be utilized to seal the interior of the bolt 10 whenever the same is not being utilized for measuring intracranial pressure.

Bolt 10 is used in the following manner. A hole 26 is first drilled in the patient's skull 12 at the appropriate position. Bolt halves 14 and 16 are separated and tubular member 20 of bolt half 14 is passed through the hole 26 with the bulbous end 28 lying just below the surface of the skull 12 and the washer 24 and flange 22 lying above the skull for sealing the same. The tubular element 36 of the upper bolt half 16 is then inserted into the interior of the lower bolt half 14. A wrench is then used to hold the lower bolt half 14 while a second wrench or similar tool is used to turn the upper bolt half 16 so that the two bolt halves are threaded together. Eventually, the lowermost end 46 of the tubular element 36 will function as a cam to flex the lowermost end 28 of the tubular member 20 outwardly to secure the bolt in position on the skull as shown in FIG. 4.

A second embodiment of the invention is illustrated in FIGS. 5–8. A subarachnoid bolt constructed in accordance with the principles of this embodiment of the invention is designated generally in FIG. 5 as 110.

As with bolt 10, bolt 110 is comprised essentially of two parts: a lower bolt half 114 and an upper bolt half 116. As shown most clearly in FIGS. 6–8, lower bolt half 114 is essentially circular in cross section except for the upper portion thereof which is squared as shown at 118 to form a means by which a wrench or similar tool 119 can hold the lower bolt half 114 to prevent the same from rotating.

The lower section of lower bolt half 114 is reduced in diameter and forms a tubular member 120 which is coaxially aligned with the remaining parts of the bolt. An enlarged flange 122 is thereby formed above the tubular member 120. A sealing washer 124 rests against the flange 122 and around the upper part of the tubular member 120.

Extending upwardly through the tubular member 120 is a hollow screw 126. The lowermost portion of the hollow screw 126 has an enlarged head 128 which abuts the extreme lower edge 130 of the tubular member 120 which prevents upward movement of the hollow screw 126. Screw 126 is long enough to extend slightly above the upper surface of the lower bolt half 114 and has this upper portion threaded as shown at 132 in FIG. 7. Adjacent the upper portion of the screw 126, one side thereof is flattened as shown at 134. This flattened portion 134 is engaged by a set screw 136 which passes through the side wall of the upper part of the lower bolt half 114. The set screw 136 does not tightly engage the flattened surface 134 of the screw 126. Rather, it is intended to prevent rotational movement of the screw 126 while allowing limited axial movement. The reasons for this will become more readily apparent hereinafter.

Figure 7:
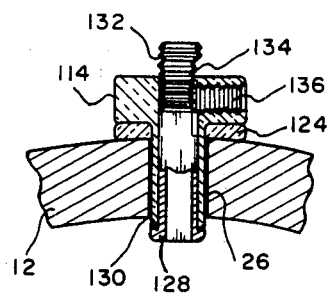
FIG. 7 is a cross-sectional view of the lower half of the bolt of FIG. 5 inserted in a hole in a patient's skull.
Figure 8:
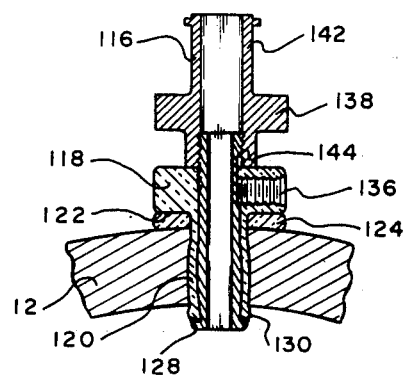
FIG. 8 is a cross-sectional view of the bolt of FIG. 5 secured to a patient's skull.

As shown most clearly in FIGS. 7 and 8, the tubular member 120 is adapted to be inserted into a substantially complementary shaped hole 26 in a patient's skull 12. The length of the tubular member 120 is selected so that the lowermost end including the lower portion 128 of the screw 126 is just below the lowermost surface of the skull 12. In this position, the flange 122 and washer 124 overlie the outer surface of the skull 12 around the hole 26 in substantially the same manner as the bolt 10 described in FIGS. 1–4.

The upper bolt half 116 is also substantially circular in cross section except for the squared section 138 which is similar in shape to the squared section 118 on the lower bolt half. The uppermost part of the upper bolt half 116 carries a coaxially arranged adapter or connector 142 which is utilized for connecting the bolt to remotely located sensing and/or measuring equipment. The lower end of the upper bolt half 116 has an internal thread 144 formed therein which is adapted to cooperate with the threaded portion 132 at the upper end of the screw 126.

Bolt 110 is used in the following manner. As with bolt 10, a hole 26 is first drilled in the patient's skull 12 at the appropriate position. Bolt halves 114 and 116 are separated and tubular member 120 of bolt half 114 is passed through the hole 26 with the lower end 128 of the screw 126 and the lower end 130 of the tubular member 120 lying just below the surface of the skull 12 and the washer 124 and flange 122 lying above the skull for sealing the same. The upper bolt half 116 is then screwed onto the lower bolt half by engaging the internal threads 144 with the external threads 132. Wrench 119 is utilized to hold the lower bolt half 114 in a stationary position while a second wrench or similar tool is used to turn the upper bolt half 116. Since the screw 126 is prevented from rotational movement by set screw 136, it is eventually drawn upwardly as the upper bolt half 116 is turned. Head 128 at the end of screw 126 engages the lower end 130 of the tubular member 120 and attempts to push this upwardly. Since the entire tubular member 120 cannot move upwardly, it eventually expands or bulges outwardly and seals tightly against the inner wall of the hole 26 in the skull 12, thus securing the bolt in position. This is clearly shown in FIG. 8.

Any suitable materials may be utilized in the manufacture of the bolts 10 and 110. In the preferred embodiments, the adapters 42 and 142 and the screws 126 and 136 are comprised of stainless steel or the like while the remaining parts of the bolt are preferably made of relatively rigid plastic. The washers are, of course, preferably comprised of a somewhat softer material so that they will produce the desired sealing function. Furthermore, the tubular member 120 must be relatively rigid but flexible enough to flex outwardly to perform its sealing function.

The present invention may be embodied in other specific forms without departing from the spirit or essential attributes thereof and accordingly, reference should be made to the appended claims rather than to the foregoing specification as indicating the scope of the invention.

I claim:

1. A subarachnoid bolt for use in measuring intracranial pressure including:
   - a lower bolt half having an upper surface and an enlarged flange and a coaxially arranged tubular member extending downwardly from said flange, said tubular member being adapted to be inserted into a substantially complementary shaped hole in a patient's skull with said flange overlying the outer surface of the skull around said hole, at least a part of said tubular member being radially expandable so that the same can be secured to the patient's skull;
   - means on said lower bolt half allowing the same to be held to prevent rotation thereof;
   - an upper bolt half including means for screwing the top to said lower bolt half, and means for causing said at least part of said tubular member to radially expand when said two bolt halves are screwed together.

2. The invention as claimed in claim 1 wherein said upper bolt half has a downwardly extending tubular element fitted within said tubular member of said lower bolt half when said upper and lower bolt halves are screwed together.

3. The invention as claimed in claim 2 wherein said lower bolt half has an opening in the upper surface thereof which is concentric with said tubular member and which has an internal screw thread therein and wherein the tubular element includes an upper end and wherein said means for screwing comprises a complementary external screw thread on said tubular element.

4. The invention as claimed in claim 1 wherein said lower bolt half includes a hollow screw pssing upwardly through the tubular member and being exposed at the upper surface of the lower bolt half.

5. The invention as claimed in claim 4 wherein said upper bolt half is screwed to the exposed portion of said hollow screw when said two bolt halves are screwed together.

6. The invention as claimed in claim 5 further including means for preventing said hollow screw from rotating when said upper bolt half is screwed onto the exposed portion thereof.

7. The invention as claimed in claim 1 wherein The tubular member is radially expandable adjacent a midpoint thereof.

* * * * *

UNITED STATES PATENT AND TRADEMARK OFFICE
CERTIFICATE OF CORRECTION

PATENT NO. : 4,572,212
DATED : February 25, 1986
INVENTOR(S) : Fred Letterio

It is certified that error appears in the above-identified patent and that said Letters Patent is hereby corrected as shown below:

Claim 1, line 18, "top" should read --same--.

Signed and Sealed this

Twelfth Day of August 1986

[SEAL]

Attest:

Attesting Officer

DONALD J. QUIGG

Commissioner of Patents and Trademarks